United States Patent
Maesani et al.

(10) Patent No.: US 12,428,363 B2
(45) Date of Patent: Sep. 30, 2025

(54) PURIFICATION OF ALIPHATIC DICARBOXYLIC ACIDS PRODUCED BY BIOTECHNOLOGICAL PROCESSES

(71) Applicant: RADICI CHIMICA S.P.A., Bergamo (IT)

(72) Inventors: Cristiano Maesani, Novara (IT); Pasquale Accorinti, Novara (IT); Stefano Alini, Cava Manara (IT)

(73) Assignee: RADICI CHIMICA S.P.A., Bergamo (IT)

( * ) Notice: Subject to any disclaimer, the term of this patent is extended or adjusted under 35 U.S.C. 154(b) by 478 days.

(21) Appl. No.: 18/005,296

(22) PCT Filed: Jul. 14, 2021

(86) PCT No.: PCT/IB2021/056334
§ 371 (c)(1),
(2) Date: Jan. 12, 2023

(87) PCT Pub. No.: WO2022/013767
PCT Pub. Date: Jan. 20, 2022

(65) Prior Publication Data
US 2023/0257336 A1    Aug. 17, 2023

(30) Foreign Application Priority Data
Jul. 16, 2020  (IT) .................. 102020000017368

(51) Int. Cl.
*C07C 51/487*    (2006.01)
*C07C 51/43*    (2006.01)
*C07C 51/47*    (2006.01)

(52) U.S. Cl.
CPC ............ *C07C 51/487* (2013.01); *C07C 51/43* (2013.01); *C07C 51/47* (2013.01)

(58) Field of Classification Search
None
See application file for complete search history.

(56) References Cited

U.S. PATENT DOCUMENTS

| | | | |
|---|---|---|---|
| 2015/0344397 A1 | 12/2015 | Kleiber et al. | |
| 2019/0248726 A1* | 8/2019 | Qin | C07C 55/21 |
| 2021/0187443 A1* | 6/2021 | Yang | B01D 9/005 |

FOREIGN PATENT DOCUMENTS

| | | |
|---|---|---|
| CN | 105 712 871 B | 10/2015 |
| WO | WO 2018/010057 | 1/2018 |

OTHER PUBLICATIONS

Machine translation of CN105712871A (Year: 2016).*
International Search Report issued Oct. 13, 2021 in connection with PCT International Application No. PCT/IB2021/056334.
Written Opinion of the International Searching Authority issued Oct. 13, 2021 in connection with PCT International Application No. PCT/IB2021/056334.

* cited by examiner

*Primary Examiner* — Medhanit W Bahta
(74) *Attorney, Agent, or Firm* — Gary J. Gershik

(57) ABSTRACT

A process for the purification of saturated linear aliphatic dicarboxylic acids, or mixtures thereof, obtained by biotechnological processes is described.

17 Claims, No Drawings

PURIFICATION OF ALIPHATIC DICARBOXYLIC ACIDS PRODUCED BY BIOTECHNOLOGICAL PROCESSES

CROSS-REFERENCE TO RELATED APPLICATIONS

This application is a § 371 national stage of PCT International Application No. PCT/IB2021/056334, filed Jul. 14, 2021, claiming priority of Italian Patent Application No. 102020000017368, filed Jul. 16, 2020, the entire contents of each of which are hereby incorporated by reference into the subject application.

FIELD OF THE INVENTION

The present invention relates to a process for the purification of saturated linear aliphatic dicarboxylic acids obtained by biotechnological processes.

STATE OF THE ART

Saturated linear aliphatic dicarboxylic acids are chemical compounds of extreme importance at an industrial level since, thanks to being bi-functional, they are widely used as monomers in the production of polymers such as polyamides, polyesters, and polyurethanes.

The production of polyamides is probably the application that requires the greatest attention to the purity of the starting monomers: impurities (e.g. mono- or polyfunctional compounds, chromophores or thermolabile compounds), even if present in trace levels, can block the polymerization, lead to branching in the polymer chain, or more generally limit the downstream applications of the polyamide. The purity requirements for monomers are particularly high when the polyamide intended use is in the textile sector (products that meet the purity requirements for use in the textile field are defined as "fiber grade").

Saturated linear aliphatic dicarboxylic acids are generally produced with traditional technologies starting from petroleum derivatives and usually leading to relatively simple mixtures of compounds, in which the desired acid is by far the majority compound. These mixtures are then subjected to purification processes developed and optimized to be effective on these simple mixtures.

In recent years, however, the chemical industry is constantly looking for productions alternative to those derived from petroleum, both to reduce dependence on this non-renewable source, and to have available processes and products which are more sustainable from an environmental and safety point of view.

Developments in biotechnology have allowed the production of compounds, including linear aliphatic dicarboxylic acids, from alternative sources, for example renewable sources such as sugars, fatty acids, vegetable oils, animal fats, or non-renewable sources such as paraffins of different chain lengths. However, the chemical quality of monomers obtained in this way is not sufficiently high to allow their extensive use in the production of polyamides, and in particular of nylons for textile applications, thus limiting their applications to the production of polymers intended for articles almost exclusively for the plastic materials sector. The main issue is related to the biological nature of the raw materials used and/or the fermentation processes applied, responsible for accumulation of chromophoric and volatile substances in the final products that tend to give a pale yellow to brown color as well as an unpleasant odor thereto.

The obtainment of a product downstream of the fermentation process takes place through two macro-phases: the first one, commonly named extraction, is aimed at recovering the product of interest from the fermentation broth, while the second one, generically named purification, consists of a series of unitary operations through which the raw product reaches the degree of purity required by the market.

In the first phase, the typical operations concern destruction and removal of cellular debris (flocculation, pasteurization, centrifugation, filtration, etc.) and the recovery of the product in a raw form (acidification, precipitation, extraction with liquids, etc.). As regards the second phase, the typical operations concern instead product purification (crystallization, distillation, passages on resins and activated carbon, chromatography, liquid-liquid extractions, etc.) and finishing (crystallization to give the desired crystalline structure, drying, freeze-drying, sterilization, etc.). The operations of this phase are generally the most complex ones and constitute the most important part of the process of obtaining compounds of interest downstream of fermentations.

The first of these two macro-phases (raw product recovery) is described in some patent publications.

U.S. Pat. No. 5,034,105 describes a process for the recovery of deprotonated succinic acid from a fermentation broth, after separation of cells and debris, by electrodialysis: using electrical energy and ion-selective membranes, sodium succinate is returned to its acid form, with simultaneous recovery of sodium hydroxide used during fermentation for pH control. The process has the advantage of not requiring neutralization with strong mineral acids and not giving rise to waste salts. Use of electricity, however, leads to non-negligible energy consumption, which increases the process costs. Furthermore, membranes, especially when working at high concentrations of organic substances, tend to get dirty, thus significantly reducing their efficiency, and making continuous washing or replacement of the same membranes necessary.

U.S. Pat. No. 6,288,275 B1 describes a technology by which it is possible to obtain a long-chain dicarboxylic acid ($>C_{12}$) directly from the fermenter without prior separation of cellular debris. According to this process, the fermentation broth is brought to a pH value below 2 by adding a strong mineral acid and then kept at a temperature of between 60 and 105° C. for up to 2 hours. Three immiscible phases are formed by decantation: an overlying organic phase containing the compound of interest, an aqueous phase in the middle, and a solid phase on the bottom of the vessel consisting of cellular debris. The addition of an organic solvent insoluble in water can favor the formation of the organic phase in which the dicarboxylic acid is dissolved; once separated from the broth, this phase is sent to the final purification. The method in this document involves prolonged exposure of the broth to high temperatures with possible significant yellowing of the same, which inevitably worsens the quality of the recovered acid.

The second macro-phase (purification and finishing of the product) is in turn described in various patent publications.

International patent application WO 2011/082378 A2 describes a method relating to a first succinic acid purification step by ion exchange resins. According to this method, it is possible to bring the ammonium succinate obtained from fermentation back to its acid form, and at the same time separate it from the inorganic salts, by passing it over a cation exchange resin, after removing cells and cellular debris upstream. Alternatively, an anion exchange resin can be used to retain the succinate and recover it later by regeneration with an acid. The acid thus obtained is then sent to further purifications to obtain the required final degree of purity. However, the intensive use of ion exchange resins leads to the need for large eluent consumption in the bed regeneration steps, with formation of large amounts of waste to be disposed of with special processes. Furthermore, the resin exchange capacity gradually declines over time, leading to the need for more and more frequent regenerations (with an increase in the amount of waste produced) or their complete replacement (with an increase in the process variable costs).

US patent application 2015/0344397 A1 describes a method using simulated moving bed chromatography (SMBC) for the purification of succinic acid from a fermentation broth, previously microfiltered/ultrafiltered and acidified with concentrated $H_2SO_4$. However, further purifications are required to obtain the final product of desired purity (through nanofiltration, using activated carbon or adsorbent resins, etc.). As the chemical-physical principle of operation of this technique is similar to the one described above, it is affected by the same issues.

U.S. Pat. No. 8,729,298 B2 also describes a method based on simulated moving bed chromatography (SMBC), in this case for the purification and separation of medium-long chain ($C_9$-$C_{18}$) dicarboxylic acids.

U.S. Pat. No. 9,517,996 B2 describes a purification process for dicarboxylic acids with chain>$C_8$ produced by fermentation, which essentially consists in lowering the pH of the broth to precipitate the long-chain dicarboxylic acids, filtering the suspension to remove the aqueous phase freed of the desired solid and cellular residues, and then subjecting the mixture of dicarboxylic acids to one or more crystallizations in an organic solvent (preferably acetic acid). The use of a monocarboxylic acid such as acetic acid as a solvent, however, entails the problem that traces of this compound can remain as impurities in the final product, acting as chain terminators in the polymerization process in which dicarboxylic acids are used.

Patent application WO 2018/010057 A1 describes a method similar to that of the previous document, wherein an acid is added to the fermentation broth to lower its pH to a value of less than 6, thus causing demulsification of the system; the obtained biphasic system is centrifuged; and the dicarboxylic acids are finally isolated from the phase containing them, for example by filtration.

Finally, patent application CN 105712871 A describes a purification method of long-chain dicarboxylic acids, comprising the steps of subjecting a fermentation broth to an acidification pre-treatment, adding concentrated sulfuric acid to the system, adding activated carbon to remove the impurities, cooling the system to precipitate crystals of long-chain dicarboxylic acids, and finally isolate the latter by filtration, followed by washing and drying.

All the processes known in the art to recover dicarboxylic acids from fermentation broths are therefore based on a sequence of physical separation (separations by filtering membranes, crystallizations, adsorbent resins, etc.) and/or ion exchange methods which, although effective, do not achieve the object of obtaining a product suitable for the most critical applications of the fiber grade.

The object of the present invention is to provide a process for the purification of saturated linear aliphatic dicarboxylic acids obtained by biotechnological processes which is exempt of defects present in the methods of the known art, and in particular which is conveniently applicable on an industrial scale.

SUMMARY OF THE INVENTION

These objects are achieved with the present invention with a process for the purification of saturated linear aliphatic dicarboxylic acids with a number of carbon atoms of between 4 and 18, or mixtures thereof, obtained from a fermentation broth, comprising the following steps:
a) removal of cells and/or cellular residues from the fermentation broth;
b) lowering the pH of the fermentation broth with precipitation of saturated linear aliphatic dicarboxylic acids and separation thereof from said broth;
c) dissolution of the crude mixture obtained in step b) containing one or more saturated linear aliphatic dicarboxylic acids and impurities in an oxidizing solution of nitric acid at a concentration of between 45 and 68% by weight at a temperature of between 60 and 100° C. for a time ranging between 0.1 and 4 hours;
d) recovery of saturated linear aliphatic dicarboxylic acids from the oxidizing solution of step c);
e) redissolution of saturated linear aliphatic dicarboxylic acids in an aqueous mixture comprising activated carbon;
f) recovery of saturated linear aliphatic dicarboxylic acids from the aqueous mixture.

DETAILED DESCRIPTION OF THE INVENTION

The present invention can be applied for the separation from a fermentation broth and subsequent purification of a saturated linear aliphatic dicarboxylic acid, or a mixture of saturated linear aliphatic dicarboxylic acids, with a number of carbon atoms of between 4 and 18, in particular between 6 and 12 carbon atoms. Since the acids are linear, the carboxyl functions are necessarily in the α and ω positions (i.e., the two terminal positions) of the carbon atom chain. Dicarboxylic acids of interest for the invention are therefore succinic acid (C4), glutaric acid (C5), adipic acid (C6), pimelic acid (C7), suberic acid (C8), azelaic acid (C9), sebacic acid (C10), undecandioic acid (C11), dodecanedioic acid (C12), brassylic acid (C13), tetradecanedioic acid (C14), pentadecanoic acid (C15), hexadecanedioic acid (C16), heptadecanoic acid (C17) and octadecanedioic acid (C18). Among these, the acids of particular interest for the purposes of the invention are adipic acid, dodecanedioic acid, or mixtures of adipic acid and suberic acid.

The dicarboxylic acid or mixture of dicarboxylic acids mentioned above are produced in a fermenter by a biotechnological process, in which a raw material that can be from a fossil source or a renewable source is fed.

Unlike the processes of the prior art, based almost exclusively on physical separation and purification methods, the process of the present invention comprises a treatment by which cellular residues and impurities that give a yellow color and odors to the final product, and are also produced during fermentation together with the saturated linear aliphatic dicarboxylic acids, are chemically degraded.

For brevity, saturated linear aliphatic dicarboxylic acids will be referred to simply as dicarboxylic acids in the remainder of the description.

The term "cellular residues" refers herein to cellular debris and biomolecules such as, for example, proteins, nucleic acids, amino acids, carbohydrates, nucleotides, peptides, etc.

In the description and in the claims, unless otherwise indicated, the amounts of components in solutions and mixtures and the concentrations of the solutions are given in percentages by weight.

For simplicity, in the following description, reference is made to one dicarboxylic acid, unless otherwise indicated, but all indications on process steps are equally valid also in the case of dicarboxylic acids mixtures.

The process of the invention includes steps a) to f).

The dicarboxylic acid is initially in the fermentation broth in which it was produced by microorganisms such as yeasts, bacteria, molds, algae, and in particular genetically modified yeasts, which are able to transform the fed raw material into the desired product. At the end of the fermentation process, in addition to these microorganisms, the fermentation broth may contain: cellular residues, sugars, vegetable oil residues, animal fats or fatty acids with a variable length ranging between C12 and C20, and dicarboxylic acids with unsaturations or any other functional group.

Dicarboxylic acids are present in the fermentation broth in a mono- or di-salt form, in which the counter ion can be any metal cation or ammonium ion, provided that it does not cause the precipitation of the compounds in the broth. Commonly, the cation associated with dicarboxylic acid is the ammonium ion. The presence of the dicarboxylic acid mono- or di-salt forms depends on the pH at which the fermentation is carried out. By exploiting the high solubility of these forms, it is possible to remove the solid parts, consisting of cells and cellular debris, from the fermentation broth.

In step a), any cellular residues and/or cells that may have remained in the broth are entirely or at least partially removed using known centrifugation and membrane filtration processes, or a combination thereof. The fermentation broth can optionally be subjected to flocculation or pasteurization operations to reduce the viscosity of the suspension. After cell removal, the broths can be further filtered with membranes having tighter cut-offs, such as for example ultrafiltration and nanofiltration membranes, or a combination thereof, in order to remove other smaller cellular residues, such as proteins, carbohydrates, nucleic acids, divalent salts, etc.

It is thus obtained a fermentation broth free from cellular residues and/or cells, or with a very small amount of cellular residues and/or cells, and containing in solution the mono- or di-salt form of the dicarboxylic acid, with a pH ranging between 4 and 8, depending on the nature of the biotechnological fermentation process employed.

In the following step b), the pH value of the broth is lowered by passing it over a strong cationic resin or by adding a strong mineral acid, such as hydrochloric acid, nitric acid or sulfuric acid, preferably nitric or sulfuric acid, down to a value of between 1.5 and 3, preferably between 1.5 and 2; this addition can be made at a temperature of between 20 and 60° C., preferably between 30 and 40° C., and under constant stirring. This acidification converts all the dicarboxylic acids present in the mixture into their free diacid form. Lowering the pH leads to almost complete precipitation of long and medium-long chain dicarboxylic acids (from C8 to C18), with low solubility in aqueous media, and to partial precipitation of partially soluble medium-short chain dicarboxylic acids (C6 and C7) and short-chain acids with an even number of carbon atoms (C4), while short-chain acids with an odd number of carbon atoms (C5) remain in solution because they are very soluble. In particular, dicarboxylic acids with solubility<5 g/L at 25° C. almost completely precipitate and can be directly subjected to filtration to remove the fermentation broth almost entirely devoid of products of interest. On the other hand, dicarboxylic acids with solubility>5 g/L at 25° C. only partially precipitate, and therefore a process to concentrate the broth by a factor of 2 to 10 times, depending on the solubility of the acid in question and the amount of water used during filtration, using a multiple-effect evaporator system or a reverse osmosis system or, preferably, a combination of these two systems, is required.

The precipitated solid is separated and removed from the residual fermentation broth, in which most of the ammonium salts produced by neutralization, chromophores, cellular residues, such as proteins, sugars and nucleic acids, remain. The obtained solid has a brownish color, rich in all the substances mentioned above and any solid cell debris not removed during the cell filtration phase, and it can be subjected to the subsequent steps of the process of the invention.

In step c) the crude dicarboxylic acid, generally in solid form, is dissolved in a nitric acid aqueous solution at a concentration of between 45 and 68%, and preferably between 50 and 65%, by weight. At these concentrations, nitric acid is a strong oxidant. Nitric acid concentrations lower than those indicated only have a reduced oxidizing action, while higher concentrations are difficult to manage in safe conditions.

The crude dicarboxylic acid is added to the nitric acid solution in such an amount that it has a concentration of between 1 and 40%, preferably between 10 and 30%, depending on its solubility in the oxidizing mixture.

The reaction temperature is of between 60 and 100° C., preferably between 70 and 90° C.: temperatures below 60° C. are inefficient in breaking down impurities, while values above 100° C. considerably accelerate corrosion of the reactor steels and lead to decomposition of nitric acid and therefore an increase in operating costs.

The reaction time can range between 0.1 and 4 hours, preferably between 0.5 and 3 hours.

Nitric acid, the oxidizing agent of the reaction, is able to attack all the molecules that are responsible for absorption of optical radiation in the visible and in the low ultraviolet (chromophoric impurities), which are generally organic molecules having one or more carbon-carbon double bonds, and in many cases conjugated double bond systems. This agent also hydrolyzes/oxidizes all cellular residues left over from fermentation, such as proteins, nucleic acids and other biological macromolecules. However, the oxidant leaves the dicarboxylic acids in the mixture unaltered, because the chain terminal carbons are already at the maximum oxidation state for an organic compound, while those in the center of the chain (without double bonds and other functional groups) are not subject to oxidation under process conditions.

The oxidation treatment can take place both discontinuously and continuously, in the latter case the reactor used can be a Continuous-flow Stirred-Tank Reactor (known in the sector as CSTR) or with a Plug Flow Reactor (or PFR), provided that the contact time is guaranteed; preferably the reactor is in continuous or batch mixing. Process gases are abated in an absorption column with known techniques, such as supply of cooled water or an alkaline solution, such as aqueous solutions of NaOH, KOH, $Ba(OH)_2$, etc., counter-current to the gas flow.

In step d) of the process, the dicarboxylic acid of interest is recovered from the oxidizing solution.

The technique used can be crystallization, preferably crystallization by cooling. The oxidizing mixture containing the dicarboxylic acid is gradually cooled until it reaches a temperature of between 10 and 40° C., preferably between 20 and 30° C., depending on the solubility of the dicarboxylic acid in question. In order to maintain a constant level of supersaturation, cooling must be slower in the first part and faster in the final part. The crystals obtained are separated from the crystallization mother liquors using well known chemical engineering techniques, such as centrifuges, drum filters, press filters, etc. Preferably, the solid is recovered by centrifugation.

The solid dicarboxylic acid is subsequently washed with demineralized water to remove the oxidant remaining between the crystals. The mother liquors can be purged and replenished with fresh oxidant in order to be used again in the oxidation reactor.

The next step of the process, e), serves to remove traces of mother liquors and impurities deriving from the oxidizing treatment from the dicarboxylic acid crystals. Since these impurities are generally responsible for an (unwanted) coloration of the dicarboxylic acids and polymers produced therewith, this treatment is also referred to as a "bleaching".

In this step, the dicarboxylic acid resulting from step d) is redissolved in water or an aqueous mixture comprising suspended activated carbon. The term "aqueous mixture" is used to indicate any solution consisting of at least 50% water.

The wet crystals are dissolved in an aqueous mixture forming a solution containing 1 to 40%, preferably 10 to 30% of dicarboxylic acid. If an aqueous mixture is used, this preferably consists of water and an organic solvent, whose amount should be carefully selected so that it is soluble in water at all process temperatures (from 20 to 100° C.). Among the organic solvents one can use, primary, secondary and tertiary alcohols, such as for example ethanol, propanol, isopropanol, butanol, tert-butanol and 2-butanol; ketones, such as for example acetone, methyl ethyl ketone, diethyl ketone; or esters such as ethyl acetate. The type of solvent and the percentage by weight should be carefully selected to minimize the possible reactivity of the solvent towards the dicarboxylic acid at the process temperature and the activated carbon, be sufficiently high boiling, guarantee low solubility of the dicarboxylic acid at temperatures between 20 and 40° C. and high solubility of the dicarboxylic acid as this parameter increases.

With dicarboxylic acids having a number of carbon atoms equal to or lower than 7, the use of water at high temperature alone is sufficient to bring the dicarboxylic acid into solution for treatment with activated carbon. With dicarboxylic acids having a number of carbon atoms equal to or greater than 8, the use of the solvent in an amount of between 0 and 50% by weight is essential to bring the dicarboxylic acid into solution and be able to perform the bleaching treatment.

The treatment is carried out at a temperature of between 60 and 100° C., preferably between 70 and 90° C. The treatment is carried out with activated carbon, preferably in powder form, by forming a stirred suspension. If powdered activated carbon is used, the amount thereof ranges between 0.5 and 50 g, preferably between 1 and 25 g per kg of dicarboxylic acid to be treated. The solution/carbon contact time ranges between 0.25 and 2 hours, preferably between 0.5 and 1.5 hours. At the end of the process, the powdered activated carbon is filtered according to methods and equipment known in chemical plant engineering and the purified solution is sent to the final product recovery step.

Finally, in step f) of the process, the discolored dicarboxylic acid is recovered from the bleaching treatment solution using known techniques such as, preferably, crystallization.

Depending on the nature of the mixture, the particle size required and the solubility of the dicarboxylic acids in the bleaching treatment solution, the crystallization is carried out by cooling, by evaporation or by adiabatic evaporation under vacuum. The solid obtained from crystallization is filtered or preferably centrifuged, continuously or discontinuously, and then washed with cold demineralized water to effectively remove the mother liquors remaining between the crystals. If a dry product is needed, the solid obtained can be sent to a drying stage to eliminate residual moisture. Drying in an inert atmosphere is particularly recommended if an organic solvent is used. The dicarboxylic acid obtained from the process described in the present invention has optical properties comparable to analogous compounds synthesized from fossil sources, and it is therefore suitable for all fields of application, even those with the most stringent quality requirements, such as the synthesis of polyamides for textile use (nylon).

The process of the invention guarantees the obtainment of high purity dicarboxylic acids, characterized by a value of <15 in the APHA scale, defined by the ASTM D1209 standard, and an absorbance value of <300 (×1000) at 275 nm, as better specified in the examples.

The invention will be further illustrated by the following examples.

Methods, Instruments and Materials

An Agilent 1260 Infinity II series HPLC instrument with G7115A diode array detector and G7162A refractive index was used to determine the composition of the fermentation broths and the final purity of the dicarboxylic acids treated in the examples. An Agilent Cary 60 UV-Vis spectrophotometer is used to determine the optical properties of the product.

Example 1

By fermenting fatty acids using the second generation genetically modified yeast *Candida viswanathii*, a broth was produced containing a mixture of dicarboxylic acids, in particular 80 g/L of adipic acid and 4.5 g/L of suberic acid in the form of monoammonium adipate and monoammonium suberate measured by HPLC analysis. Cells and other solids were removed by ultrafiltration/diafiltration (an Alfa-Laval RC70PP ultrafiltration membrane made of spiral wound regenerated cellulose, 80 mil spacers equivalent to 2 mm, 10 kDa cut-off was used), producing a clarified broth free of any cellular debris with a concentration of 35.8 g/L of adipic acid and 1.96 g/L of suberic acid in their mono-salt forms, determined also in this case by HPLC analysis. 1700 g of broth were acidified with $HNO_3$ at 65% by weight (Radici Chimica SpA) until a pH of 1.8 is reached. Acidification displaced monoammonium adipate and suberate into their acid forms, namely adipic acid and suberic acid. Since adipic acid, the main product, is partially soluble in water, a 7× concentration of the broth by evaporation was performed up to a 25.1% by weight concentration of this compound. Once cooled to room temperature (20° C.), most of the acid precipitated and the crystals were filtered and washed with demineralized water. These were subsequently dissolved in 55% concentrated nitric acid (Radici Chimica SpA), brought to 80° C. and kept under stirring for 2 hours. The concentration of the wet solid in the nitric solution was equal to 30% by weight. At the end of the oxidation, the mixture was left to crystallize by cooling it down to 25° C., and then filtered on a porous septum. The crystals obtained were washed twice with demineralized water in an amount of 1:1 by weight with respect to the wet crystals. The wet product obtained was subsequently redissolved in water and brought to 85° C., thus forming a 30% by weight solution of dicarboxylic acids with respect to the wet product. Powdered activated carbon (Ceca, 65% by mass of which has a particle size<40 μm) was added to the solution in an amount equal to 3.33 g of carbon per kg of dicarboxylic acid mixture, and the solution was then kept under constant stirring for 60 minutes. At the end of the treatment, the carbon was hot-filtered on a büchner funnel and the solid-free solution was crystallized by cooling it down to 20° C. The crystals were separated from the mother liquors by means of a porous septum, washed with demineralized water, and dried in oven at 70° C. for 24 hours. The recovery yield as total solid (sum of the two acids) with respect to the starting one is of 68.9% and the crystals obtained had a composition, measured by HPLC, consisting of 96.4% adipic acid and 3.3% by weight of suberic acid (the remainder is residual moisture). The dry crystals were analyzed by spectrophotometer for determination of the optical properties. 7.66 g of powder were dissolved in 60 g of ammonia solution at 5% by weight, carefully filtered with a syringe filter and analyzed on the Agilent Cary 60 spectrophotometer with a quartz cuvette having an optical path of 50 mm. An absorbance ×1000 at 275 nm equal to 117 and an APHA color at 390 nm equal to 7.4 were obtained.

Example 2

1900 g of the same ultrafiltered broth described in example 1 were purified using the same process. However, the nitric acid treatment was made to last 30 minutes instead of 2 hours. The recovery yield of the two acids was of 69.2% and the crystals obtained had a composition measured by HPLC consisting of 97.14% adipic acid with the remaining part being suberic acid. The dry crystals were analyzed on the spectrophotometer to determine the optical properties. 7.66 g of powder were dissolved in 60 g of ammonia solution at 5% by weight, carefully filtered with a syringe filter and analyzed using an Agilent Cary 60 spectrophotometer with a quartz cuvette having an optical path of 50 mm. An absorbance ×1000 at 275 nm equal to 107 and an APHA color at 390 nm equal to 6.9 were obtained.

Example 3

1600 g of the same ultrafiltered broth described in example 1 were purified using the same process. The nitric acid treatment was carried out with a nitric solution at 65% rather then 55%, by weight. The recovery yield of the two acids was of 64% and the crystals obtained had a composition measured by HPLC consisting of 98.3% adipic acid with the remaining part being suberic acid. The dry crystals were analyzed on the spectrophotometer to determine the optical properties. 7.66 g of powder were dissolved in 60 g of ammonia solution at 5% by weight, carefully filtered with a syringe filter and analyzed using an Agilent Cary 60 spectrophotometer with a quartz cuvette having an optical path of 50 mm. An absorbance ×1000 at 275 nm equal to 86 and an APHA color at 390 nm equal to 5.2 were obtained.

Example 4

A sample of the fermentation broth described in example 1 was ultrafiltered/diafiltered for cell removal and subsequently nanofiltered/diafiltered (SUEZ GE DL, polyamide TFC, spiral wounds; cut-off 150-300 Da) to remove the biological macromolecules such as proteins and sugars, divalent salts and most of colored impurities. The adipic acid concentration in the nanofiltrate was of 31.57 g/L, while that of suberic acid was of 1.95 g/L, as measured by HPLC. 1900 g of this broth were purified using the same process described in example 1. The recovery yield of the two acids was of 61.7% and the crystals obtained had a composition measured by HPLC consisting of 96.4% acid adipic acid and 3.36% suberic acid (with the remainder being moisture). The dry crystals were analyzed on the spectrophotometer to determine the optical properties. 7.66 g of powder were dissolved in 60 g of ammonia solution at 5% by weight, carefully filtered with a syringe filter and analyzed using an Agilent Cary 60 spectrophotometer with a quartz cuvette having an optical path of 50 mm. An absorbance ×1000 at 275 nm equal to 134 and an APHA color at 390 nm equal to 5.4 were obtained.

Example 5

By fermenting fatty acids using the second generation genetically modified yeast Candida viswanathii, a broth containing 50 g/L of adipic acid in the form of mono ammonium salt was produced, as measured by HPLC. At the end of the fermentation, 1800 g of broth were centrifuged and most of the cells and solid residues were eliminated. The fermentation broth described, which still contained a small portion of cellular solid, was purified using the same method reported in example 1. The recovery yield of the product was 71.7% and the crystals obtained had a composition measured by HPLC consisting of 99.7% adipic acid (with the remainder being moisture). The dry crystals were analyzed on the spectrophotometer to determine the optical properties. 7.66 g of powder were dissolved in 60 g of ammonia solution at 5% by weight, carefully filtered with a syringe filter and analyzed using an Agilent Cary 60 spectrophotometer with a quartz cuvette having an optical path of 50 mm. An absorbance ×1000 at 275 nm equal to 84 and an APHA color at 390 nm equal to 5.1 were obtained.

A summary table of the results obtained in the tests performed is reported below.

| Example | Starting broth used | Oxidation Conditions | APHA color (390 nm) | Absorbance at 275 nm (×1000) |
|---|---|---|---|---|
| 1 | Ultrafiltrated | 55% HNO$_3$ - 2 hrs | 7.4 | 117 |
| 2 | Ultrafiltrated | 55% HNO$_3$ - 0.5 hrs | 6.9 | 107 |
| 3 | Ultrafiltrated | 65% HNO$_3$ - 2 hrs | 5.2 | 86 |
| 4 | Nanofiltrated | 55% HNO$_3$ - 2 hrs | 5.4 | 134 |
| 5 | Centrifugated | 55% HNO$_3$ - 2 hrs | 5.1 | 84 |

The invention claimed is:
1. A process for the purification of saturated linear aliphatic dicarboxylic acids with a number of carbon atoms of between 4 and 18, or mixtures thereof, obtained from a fermentation broth, comprising the following steps:
 a) removal of cells and/or cellular residues from the fermentation broth;
 b) lowering the pH of the fermentation broth with precipitation of saturated linear aliphatic dicarboxylic acids and separation thereof from said broth obtaining a crude mixture containing one or more saturated linear aliphatic dicarboxylic acids and impurities;
 c) dissolution of the crude mixture obtained in step b) in an oxidizing solution of nitric acid at a concentration of between 45 and 68% by weight at a temperature of between 60 and 100° C. for a time ranging between 0.1 and 4 hours;
 d) recovery of saturated linear aliphatic dicarboxylic acids from the oxidizing solution of step c);
 e) redissolution of saturated linear aliphatic dicarboxylic acids in an aqueous mixture comprising activated carbon at a temperature of between 60 and 100° C.;

f) recovery of saturated linear aliphatic dicarboxylic acids from the aqueous mixture.

2. The process according to claim 1, wherein said saturated linear aliphatic dicarboxylic acids have a number of carbon atoms of between 6 and 12.

3. The process according to claim 2, wherein said acids are selected from adipic acid, dodecanedioic acid and mixtures of adipic acid and suberic acid.

4. The process according to claim 1, wherein step a) is carried out by centrifugation and/or membrane filtration.

5. The process according to claim 1, wherein in step b) the pH is brought to a value of between 1.5 and 3 with a strong mineral acid, operating at a temperature of between 20 and 60° C.

6. The process according to claim 1, wherein step b) is favored by concentrating the broth by a factor of 2 to 10 with the use of a multiple-effect evaporator system and/or a reverse osmosis system.

7. The process according to claim 1, wherein the nitric acid aqueous solution used in step c) has a concentration of between 50 and 65% by weight.

8. The process according to claim 1, wherein in step c) the crude mixture obtained in step b) is added to the nitric acid solution in an amount such that its concentration in the resulting solution is of between 1 and 40% by weight.

9. The process according to claim 1, wherein step c) is carried out at a temperature of between 70 and 90° C. for a time ranging between 0.5 and 3 hours.

10. The process according to claim 1, wherein step d) is carried out by crystallization of the dicarboxylic acids present in the oxidizing mixture and subsequent separation of the crystals from the mixture by centrifugation or filtration.

11. The process according to claim 1, wherein step e) is carried out at a temperature of between 70 and 90° C., dissolving the dicarboxylic acid crystals recovered in step d) in water or an aqueous mixture comprising powdered activated carbon in suspension in an amount of between 0.5 and 50 g per kg of dicarboxylic acids to be treated, wherein said aqueous mixture comprises at least a second component selected from a primary, secondary or tertiary alcohol, a ketone and an ester.

12. The process according to claim 1, wherein step f) is carried out by crystallization.

13. The process according to claim 3, wherein step a) is carried out by centrifugation and/or membrane filtration.

14. The process according to claim 13, wherein in step b) the pH is brought to a value of between 1.5 and 3 with a strong mineral acid, operating at a temperature of between 20 and 60° C.

15. The process according to claim 14, wherein step b) is favored by concentrating the broth by a factor of 2 to 10 with the use of a multiple-effect evaporator system and/or a reverse osmosis system.

16. The Process according to claim 15, wherein the nitric acid aqueous solution used in step c) has a concentration of between 50 and 65% by weight.

17. The process according to claim 16, wherein in step c) the crude mixture obtained in step b) is added to the nitric acid solution in an amount such that its concentration in the resulting solution is of between 1 and 40% by weight.

* * * * *